US00PP36030P2

(12) United States Plant Patent
Trees

(10) Patent No.: US PP36,030 P2
(45) Date of Patent: Jul. 23, 2024

(54) ***HYDRANGEA* PLANT NAMED 'OAKANN1588'**

(50) Latin Name: *Hydrangea quercifolia*
Varietal Denomination: Oakann1588

(71) Applicant: The Conard Pyle Company, West Grove, PA (US)

(72) Inventor: Scott Trees, Arroyo Grande, CA (US)

(73) Assignee: The Conard Pyle Company, West Grove, PA (US)

( * ) Notice: Subject to any disclaimer, the term of this patent is extended or adjusted under 35 U.S.C. 154(b) by 26 days.

(21) Appl. No.: 18/203,780

(22) Filed: May 31, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP25,106 P2 * 11/2014 Hill ..... A01H 6/48
Plt./250

OTHER PUBLICATIONS

Star Roses and Plants, retrieved on Sep. 14, 2023 at https://www.starrosesandplants.com/plants/lil-annie-oakleaf-hydrangea/, 4 pp. (Year: 2023).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct cultivar of *Hydrangea* plant, referred to by its cultivar name, 'Oakann1588', is disclosed. The new variety forms attractive, white colored inflorescences that age to pink. Medium green colored foliage forms. A moderately vigorous, well branched, mounding, and compact growth habit is displayed. The new variety is well suited for providing attractive ornamentation in the landscape.

1 Drawing Sheet

Latin name of genus and species of plant claimed: *Hydrangea quercifolia.*

Variety denomination: 'Oakann1588'.

STATEMENT REGARDING PRIOR DISCLOSURES BY THE INVENTOR

The first offer for sale of the new variety was June 2022, in the United States of America. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new cultivar originated in Guadalupe, California in 2013. The new *Hydrangea* cultivar is the result of cross-pollination. The female (seed) parent of the new cultivar is a *Hydrangea quercifolia* unnamed variety, not patented. The male (pollen) parent of the new cultivar is unknown. The new cultivar was discovered and selected as a single flowering plant within the progeny of the above stated cross-pollination in Guadalupe, California.

The new variety has been found to undergo asexual propagation in Cochranville, Pennsylvania by terminal stem cuttings since July 2017. Asexual propagation by terminal stem cuttings in Cochranville, Pennsylvania has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Hydrangea* plant of the present invention possesses the following combination of characteristics:

(a) forms white colored inflorescences that age to pink,
(b) exhibits medium green colored foliage, and
(c) displays a moderately vigorous, well branched, mounding, and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, plants of the new cultivar differ from plants of the female parent (i.e., the seed parent) primarily in that the new cultivar is more compact with a better branching habit and lighter green colored foliage.

Moreover, the new variety can be readily distinguished from other similar non-parental varieties. Of the many commercially available *Hydrangea* cultivars, the most similar in comparison to the new cultivar is 'Ruby Slippers', (not patented) However, in comparison, plants of the new cultivar differ from plants of 'Ruby Slippers' at least because the new cultivar blooms earlier than the 'Ruby Slippers' variety and plants of the new cultivar express less susceptibility to foliar disease than plants of 'Ruby Slippers'.

BRIEF DESCRIPTION OF THE PHOTOGRAPHS

The accompanying photograph shows, as nearly true as it is reasonably possible to make the same in color illustrations of this type, typical flower and foliage characteristics of a plant of the new cultivar. Colors in the photographs differ slightly from the color values cited in the detailed description, which accurately describes the colors of 'Oakann1588'. The plant of the new cultivar was approximately four years old and was observed in July 2021, while growing in a field at Cochranville, Pennsylvania, U.S.A.

The drawing sheet illustrates the overall growth and flowering habit of a plant of 'Oakann1588'.

DETAILED BOTANICAL DESCRIPTION

The chart used in the identification of the colors is that of The Royal Horticultural Society (The R.H.S. Colour Chart, 2015 edition), London, England, except where general color terms of ordinary significance are used. The terminology which precedes reference to the chart has been added to indicate the corresponding color in more common terms and The R.H.S. Colour Chart designation used herein represents the closest color observed on the majority of the specified botanical feature. The color values were determined in July 2022, under natural light conditions in Cochranville, Pennsylvania. The terminology which precedes reference to the chart has been added to indicate the corresponding color in more common terms. The description is based on the observation of plants produced from cuttings from stock plants and grown in three-gallon containers utilizing a soilless growth medium for 1 year in an outdoor nursery in Cochranville, Pennsylvania. Measurements and numerical values represent averages of typical plants.

Botanical classification: *Hydrangea quercifolia* cultivar 'Oakann1588'.

Parentage:

*Female parent.*—A *Hydrangea quercifolia* unnamed variety, not patented.

*Male parent.*—Unknown.

Propagation:

*Type cutting.*—Softwood cuttings.

*Time to initiate roots during the summer.*—Approximately 28 days.

*Time to produce a rooted young plant, summer.*—Approximately four months.

*Root description.*—White, medium thickness, fibrous.

*Rooting habit.*—Moderate branching and density.

Plant description:

*Commercial crop time.*—Approximately 12 months from a rooted cutting to finish in a 3-gallon pot.

*Growth habit and general appearance.*—Deciduous shrub, mounding compact plant habit; strong and sturdy lateral branches; freely branching dense habit; moderately vigorous growth habit — the average amount of plant growth per season is about 12 inches.

*Hardiness.*—USDA Zone 5 (−20° F. to −15° F.).

*Size.*—Height from soil level to top of plant plane: Approximately 57.0 cm. Width: Approximately 72.0 cm.

*Branching habit.*—Freely branching. Pinching enhances branching. Quantity of lateral branches per plant: Approximately 4.

*Branch.*—Shape: Rounded. Strength: Strong. Length of lateral branch: Approximately 36.0 cm. Diameter: Approximately 7.0 mm. Length of central internode: Approximately 4.0 cm. Texture of young stem: Glabrous. Texture of mature stem: Woody. Color of young stem: Greyed-Orange Group 177B. Color of mature stem: Brown Group 200B. Size of stem's lenticle: Approximately 1.0 mm in diameter. Shape of stem's lenticle: Circular. Color of stem's lenticle: Greyed-Orange Group 165C. Mature surface texture of exfoliating bark: Cracked and papyraceous. Color of exfoliated bark: Brown Group 200A.

Foliage description:

*General description.*—Quantity of leaves per lateral branch: 16 on average. Fragrance: None detected. Form: Simple. Arrangement: Opposite.

*Leaves.*—Aspect: Flat. Shape: Ovate. Margin: Lobed with serrulation. Number of leaf lobes: 5 per leaf. Apex: Acuminate. Base: Obtuse. Venation pattern: Pinnate. Length of mature leaf: Approximately 13.0 cm. Width of mature leaf: Approximately 9.0 cm. Texture of upper surface: Leathery; pubescent. Texture of lower surface: Coarse; pubescent. Color of upper surface of young foliage: Green Group 137B with indistinguishable venation. Color of lower surface of young foliage: Green Group 138C with indistinguishable venation. Color of upper surface of mature foliage: Yellow-Green Group 146A with venation Green Group 139D. Color of lower surface of mature foliage: Yellow-Green Group 147B with venation Yellow-Green Group 145A. Color of upper surface in the fall: Greyed-Purple Group 187A with indistinguishable venation. Color of lower surface in the fall: Greyed-Purple Group N186C with venation Greyed-Purple Group N186D. Dormant terminal leaf bud shape: Conical with two pairs of decussate leaves. Dormant terminal leaf bud size: Typically 1.9 cm to 2.6 cm tall and approximately 0.8 cm in diameter. Dormant terminal leaf bud color: a color between Greyed-Orange Group 167D and 165B.

*Petiole.*—Length: Approximately 7.0 cm. Diameter: Approximately 4.0 mm. Texture of upper and lower surfaces: Pubescent. Color of upper surface: Greyed-Orange Group 176D. Color of lower surface: Yellow-Green Group 145B.

Flowering description:

*Flower type and habit.*—Single sterile and fertile flowers arranged on large terminal mophead-type panicles, flowers face upright or outwardly.

*Fragrance.*—Strongly fragrant; pleasant.

*Natural flowering season.*—Seasonal, May through August.

Inflorescence description:

*General description.*—Height: Approximately 13.0 cm. Width: Approximately 9.0 cm. Shape: Conical.

Quantity of fertile florets per inflorescence: Approximately 320. Quantity of sterile florets per inflorescence: Approximately 38; range from about 30 to 80; older plants tend to have a higher number of florets per inflorescence.

Flower description:

*Fertile flowers.*—Flower diameter: About 8.0 mm. Flower depth (height): About 4.0 mm. Flower bud length: About 2.0 mm. Flower bud diameter: About 1.0 mm. Flower bud shape: Obovate. Flower bud color: Yellow-Green Group 154C. Petal arrangement: Five in a single whorl. Petal length: About 1.0 mm. Petal width: About 0.5 mm. Petal Shape: Elliptic. Petal apex: Obtuse. Petal base: Cuneate. Petal Margin: Entire. Petal texture of upper and lower surfaces: Smooth, glabrous. Petal color when opening of upper and lower surfaces: Yellow-Green Group 145B. Petal color when fully opened of upper and lower surfaces: Yellow-Green Group 145B. Sepals: Quantity per flower: Five in a single whorl. Length: About 0.5 mm. Width: About 0.5 mm. Shape: Subulate. Apex: Acute. Base: Cuneate. Margin: Entire. Texture, upper and lower surfaces: Smooth, glabrous. Color: When opening, upper and lower surfaces: Yellow-Green Group 144B. Fully opened, upper and flower surfaces: White Group 155A. Pedicel Angle: About 20 to 45 degrees from vertical. Pedicel strength: Strong, sturdy. Pedicel length: About 5.0 mm. Pedicel diameter: About 1.0 mm. Pedicel texture: Pubescent. Pedicel color: Greyed-Orange Group 176A. Conspicuousness of fertile flowers within the inflorescence: Medium.

*Sterile flowers.*—Flower diameter: About 3.3 cm. Flower depth (height): About 2.0 mm. Flower bud length: About 3.0 mm. Flower bud diameter: About 2.0 mm. Flower bud shape: Obovate. Flower bud color: Yellow-Green Group 154C. Sepals: Quantity per flower: Four in a single whorl. Attitude of Sepals: Horizontal. Intensity of overlapping Sepals: Medium. Sepal Length: About 1.5 cm. Sepal Width: About 1.4 cm. Shape: Orbicular. Apex: Obtuse. Base: Obtuse. Margin: Entire. Texture, upper surface: Smooth, glabrous. Texture, lower surface: Coarse, glabrous. Color: When opening, upper and lower surfaces: Yellow Group 4D. Fully opened, upper and lower surfaces: White Group 155A. Aged (generally around middle of July): ranges from Red-Purple Group 58A to 65C. When fading or aging during cooler temperature: ranges from Red-Purple Group 58A to 65C. Pink coloration of aged cover the entire inflorescence. Pedicel Angle: 20 to 40 degrees from vertical. Pedicel strength: Strong, sturdy. Pedicel length: About 2.5 cm. Pedicel diameter: About 1.0 mm. Pedicel texture: Smooth. Pedicel color: Yellow-Green Group 145C.

*Reproductive organs, fertile flowers.*—Stamens: Quantity per flower: About 8. Filament amount: About 4.0 mm. Filament color: White Group 155D. Anther shape: Round. Anther length: About 0.5 mm. Anther color: Greyed-Orange Group 166D. Pollen amount: None observed. Pistils: Pistil quantity per flower: About three. Pistil length: About 3.0 mm. Stigma shape: Round. Stigma color: White Group 155D. Style length: About 2.0 mm. Style color: White Group 155D. Ovary color: Green Group 138B.

Development:

*Seed and fruit production.*—Neither seed nor fruit production has been observed.

*Disease and pest resistance.*—Very good resistance to leaf spot (*Cercospora hydrangeae*). Resistance to pests common to *Hydrangea* has not been observed.

The new cultivar has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct variety of *Hydrangea* plant named 'Oakann1588' characterized by the following combination of characteristics:

(a) forms white colored inflorescences that age to pink, (b) exhibits medium green colored foliage, and (c) displays a moderately vigorous, well branched, mounding, and compact growth habit;

substantially as herein shown and described.

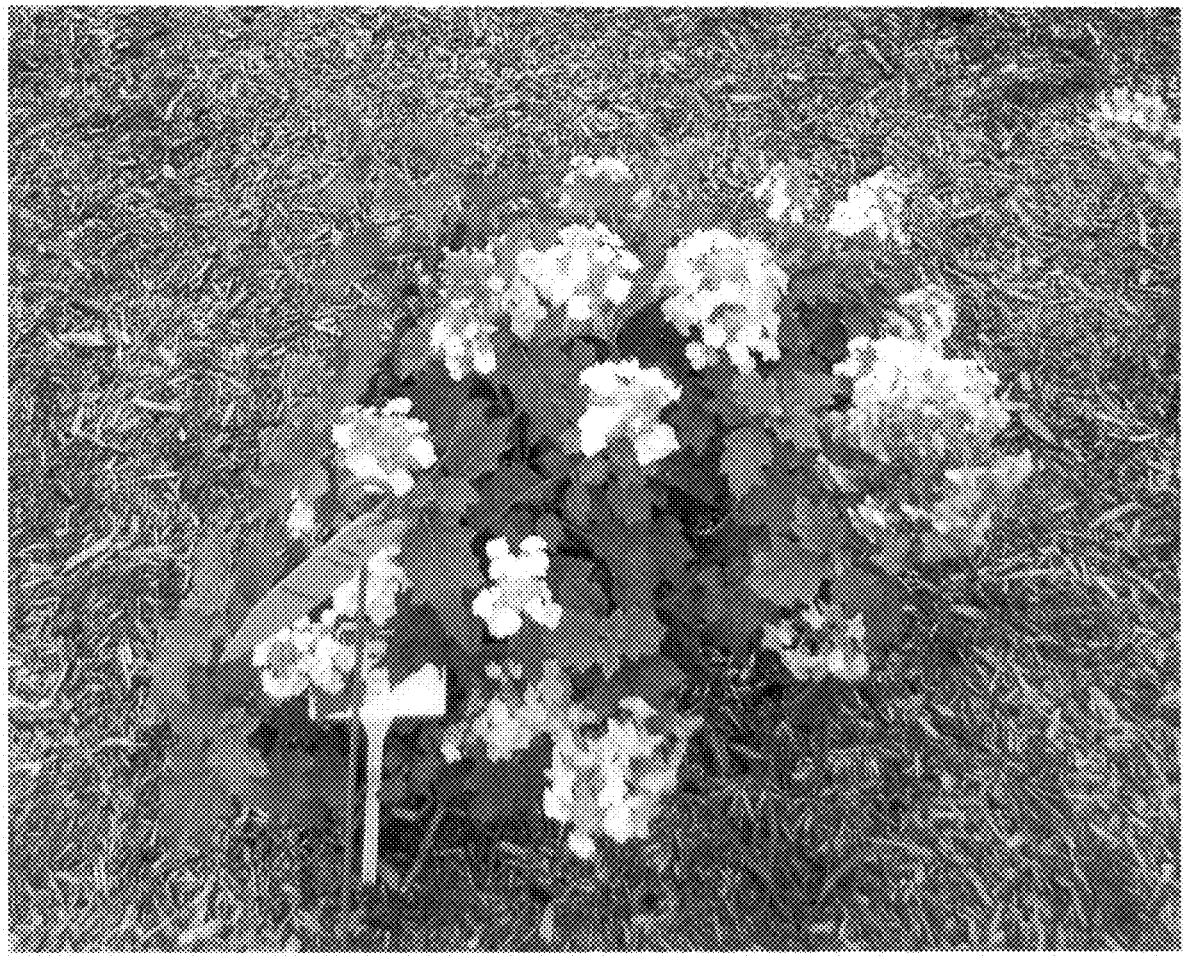

* * * * *